(12) United States Patent
Andersson (10) Patent No.: US 6,796,969 B1
(45) Date of Patent: Sep. 28, 2004

(54) HYPODERMIC INJECTION DEVICE (76) Inventor: Stig O. Andersson, 16165 Joplin Ave., Lakeville, MN (US) 55044

( * ) Notice: Subject to any disclaimer, the term of this patent is extended or adjusted under 35 U.S.C. 154(b) by 266 days.

(21) Appl. No.: 10/113,122

(22) Filed: Mar. 29, 2002

Related U.S. Application Data (60) Provisional application No. 60/279,816, filed on Mar. 29, 2001.

(51) Int. Cl.[7] .............................. A61M 5/32; A61M 5/00
(52) U.S. Cl. ........................................ 604/198; 604/110
(58) Field of Search ................................ 604/110, 195, 604/197, 198; 128/919

(56) References Cited

U.S. PATENT DOCUMENTS

| | | | |
|---|---|---|---|
| 5,147,303 A | | 9/1992 | Martin |
| 5,190,526 A | | 3/1993 | Murray et al. |
| 5,211,628 A | | 5/1993 | Marshal |
| 5,324,265 A | | 6/1994 | Murray et al. |
| 5,395,346 A | | 3/1995 | Maggioni |
| 5,411,487 A | | 5/1995 | Castagna |
| 5,569,203 A | | 10/1996 | Chen |
| 6,033,385 A | * | 3/2000 | Liu ............................ 604/195 |
| 6,193,695 B1 | * | 2/2001 | Rippstein, Jr. .............. 604/195 |
| 6,413,236 B1 | * | 7/2002 | Van Dyke ................... 604/110 |
| 2001/0021821 A1 | | 9/2001 | Wang et al. |
| 2001/0031940 A1 | | 10/2001 | Loos |
| 2001/0037088 A1 | | 11/2001 | Domici, Jr. et al |
| 2001/0044599 A1 | | 11/2001 | Lo |
| 2002/0010422 A1 | | 1/2002 | Du Plessis |

* cited by examiner

Primary Examiner—Michael J. Hayes
(74) Attorney, Agent, or Firm—Gray Plant Mooty Mooty and Bennett, P.A.; Malcom D. Reid (57) ABSTRACT A hypodermic injection device comprised of a barrel with an open end, an annular barrel grip at the open end, a luer sleeve at the distal end, a septum in the luer sleeve, and a guide-way in alignment with the central axis of the barrel extending through a guide-way in the luer sleeve. The injection device also comprises a piston in alignment with the central axis engaged for sliding movement within the barrel. The piston has a lock attached to the piston for depression of the lock into a depression space so the piston may be extended into the barrel and for return of the lock to a raised position upon release of depression pressure to allow the piston to be again locked from axial extension into the barrel. The piston also has a faceplate on its distal end with a hook at its periphery for hooking a support plate when the piston is turned within the barrel. The faceplate has a convex location boss on its distal face for mating engagement with a concave location boss on a proximal face of the support plate and for disengagement with the concave location boss when the piston is turned within the barrel to hook the support plate. The support plate supports the proximal end of the needle and has an undercut for engagement with the hook when the piston is turned within the barrel. The distal end of the needle is supported a guide-way, the needle having a length such that when the piston is retracted out of the barrel beyond a locked position, the distal end of the needle retracts from the guide-way and is contained within the reservoir.

13 Claims, 9 Drawing Sheets

HYPODERMIC INJECTION DEVICE

CROSS REFERENCE TO A RELATED APPLICATION

This application claims the benefit of U.S. Provisional Patent Application Ser. No. 60/279,816, filed Mar. 29, 2001.

BACKGROUND OF THE INVENTION

2. Field of Use

The field of use for the hypodermic injection device described herein is for injecting fluids into or withdrawing fluids from living or non-living organisms or inanimate objects, all of the foregoing generically referred to a thing 68 or sometimes as a body. With respect to living or nonliving organisms, the hypodermic injection device is generally used for injecting medicine into the body or withdrawing fluids from the body. Frequently, injections are made into subcutaneous tissues and fluids are withdrawn from cavities within the body. Although, the major use of the hypodermic injection device will most likely be in connection with the treatment of humans and human cadavers; application of the device will also be found in connection with other animals and their cadavers and also plants. Uses of the device will also be found in connection with inanimate articles and materials. For illustration purposes only, the description of this invention will center around use of the hypodermic injection device in connection with the treatment of humans.

3. Description of the Related Art

There are many hypodermic injection devices on the market today. These devices are ubiquitous in the medical arts. They are used in both the clinical and surgical settings. Hypodermic injection devices suffer from several shortcomings. The extended needle poses a hazard to both the medical caregiver and the patient from accidental needle pricks. The devices do not have a nearly fail-safe method of self-destruction after use; thereby allowing possible reuse and the concomitant transmission of disease. Disposal of the injection device also poses some risk of accidental needle pricks due to the extension of the islet or needle portion of the used injection device. The exposed islet also necessitates special disposal containers for sharp contaminated articles. Furthermore, hypodermic injection devices rarely feature a safety mechanism for locking the injection device so that fluid may not be accidentally expelled, and when they do the safety mechanism is not easy and fast to use during surgery, for example.

SUMMARY OF THE INVENTION

Today with the proliferation of many blood borne contagious diseases such as AIDS and Ebola, the frequent use of hypodermic injection devices poses a serious threat of infection. This is especially true in the surgical setting. Surgery is usually a team effort. It often requires the use of multiple hypodermic injections or the withdrawal of fluids from a patient. It is not uncommon for surgery to take place under emergency conditions. All of these factors combine to set the stage for accidental needle pricks to surgical team members with the attendant uncertainty of possible infection. Many times, it is not possible to determine for an extended period of time whether the caregiver has been infected as a result of a needle prick. The result can be actual infection with a lethal blood borne pathogen or a prolonged period of anguish and worry only to discover that the caregiver is not infected. Besides the anguish, the care giver is not infrequently side-lined from performing surgery for fear that he/she may in fact be infected and may transmit the disease to a patient or other member of the surgical team. While the surgical arena presents the highest level of accidental needle pricks, other more pedestrian areas of medical practice also present significant risks, such as in the every-day clinical practice of medicine.

It has long been recognized that the needle prick risk factor needs to be controlled. Training and care while using hypodermic needles is emphasized. But, this, in of itself, is not enough, considering the high probability of a needle prick and the disastrous level of damage to health that it can inflict upon both the patient and caregiver.

It is common practice in the health care industry to use a hypodermic injection device only once and then to dispose of it in a safe manner. However, it is also well known that intravenous drug users often reuse hypodermic injection devices and share them with other users. This, of course, is one of the major reasons for the high prevalence of AIDS and other blood borne infections among such drug users. It is also a major cause of infection of the sexual partners of intravenous drug users. The hypodermic injection device of the present invention is designed to be a single use device. Any attempt to refill the injection device results in retraction of the needle into the fluid reservoir in the barrel of the injection device. The nozzle end of the needle then drops into the reservoir of the injection device making it virtually impossible to extend the needle through the guide-way and outside of the barrel. With the needle tilted into the distal end of the reservoir, it is simultaneously disabled from further use and is safely disposed of, thereby avoiding transmission of blood borne infections by needle sharing and accidental needle sticks. Furthermore, in both the clinic and hospital settings, the disposal of the injection device is much safer and may require a less costly sharps disposal method or device than currently required.

The present invention features a normally retracted needle. This alone reduces risk of accidental needle pricks, since the needle is not exposed so it can injure anyone until it is actually ready to be filled with the injected fluid or to be used for withdrawing fluids.

The present invention also features a locking mechanism that does not allow the needle to be accidentally extended beyond the barrel of the injection device. Extension of the needle requires the user to deliberately depress the tab-like lock, which is integrally molded into the piston. Depression of the lock into the lock depression space in the piston allows the lock to clear the inside diameter of the barrel, allowing the piston to travel in axial alignment into the barrel and thereby extend the needle beyond the distal end of the luer sleeve.

The hypodermic injection device is also amenable to cost-effective manufacture by injection molding. Its novel structure is uncomplicated. And, its method of use is straightforward. One of the components of an embodiment of the injection device is a barrel with an open end, barrel grip, a luer sleeve at the distal end of the barrel in alignment with the central axis of the barrel, an end cap and a septum in the distal end of the luer sleeve, and a guide-way through the luer sleeve in alignment with the central axis. Another component of this embodiment is a piston in alignment with the central axis engaged for axial sliding movement within the inner wall of the barrel. The piston also comprises a lock attached to the piston by a tab for depression into a depression space of a depth to allow the lock to be flush with the diameter of the piston so the piston may be extended into the barrel and the lock may return to a normal raised position upon release of depression pressure to allow the piston to be locked from further axial extension into the barrel. The distal end of the piston has a faceplate with a hook at its periphery for hooking a support plate when the piston is turned within the barrel. The faceplate also has a convex location boss on its distal face for engagement with a concave location boss on a proximal face of the support plate and for disengagement with the concave location boss when the piston is turned within the barrel to hook the support plate. The support plate supports a needle on the central axis, the bore of the needle in communication with an inlet and an undercut for engagement with the hook when the piston is turned within the barrel. The distal end of the needle is supported in the guide-way, the needle having a length such that when the piston is retracted out of the barrel beyond a locked position with respect to the barrel, the needle retracts from the guide-way so that the distal end of the needle is contained within the reservoir. The reservoir is located in the distal end of the barrel when the piston is in the locked position in the barrel. The length of the reservoir is directly related to the longitudinal distance of the location of the lock on the piston from the faceplate.

The above described embodiment of the hypodermic injection device is used in the following manner: (a) with the piston of the injection device in a first position wherein the piston is locked into longitudinally position with respect to the barrel and the distal end of the needle is supported in the needle guide-way, the lock is depressed and then the piston is slid in a distal direction into the barrel to the distal end of the barrel, so that the needle is extended beyond the distal end of the end cap; (b) the needle is extended into a fluid to be injected; (c) the piston is retracted in the proximal direction until the lock engages the proximal end of the barrel, so that the fluid is drawn into the reservoir; (d) the needle is inserted into the thing to be injected; (e) the lock is depressed and then the piston is slid in a distal direction into the barrel to the distal end of the barrel, so that the fluid in the reservoir is injected into the thing to be injected; (f) the piston is turned in the barrel to engage the piston hook with the support plate undercut; and (g) the piston is retracted from the barrel in a proximal direction to a point where the lock is beyond the barrel open end, so that the distal end of the needle is within the reservoir.

DETAILED DESCRIPTION AND OPERATION OF AN EMBODIMENT OF THE INVENTION

1. Detailed Description of Invention

Figure 1:
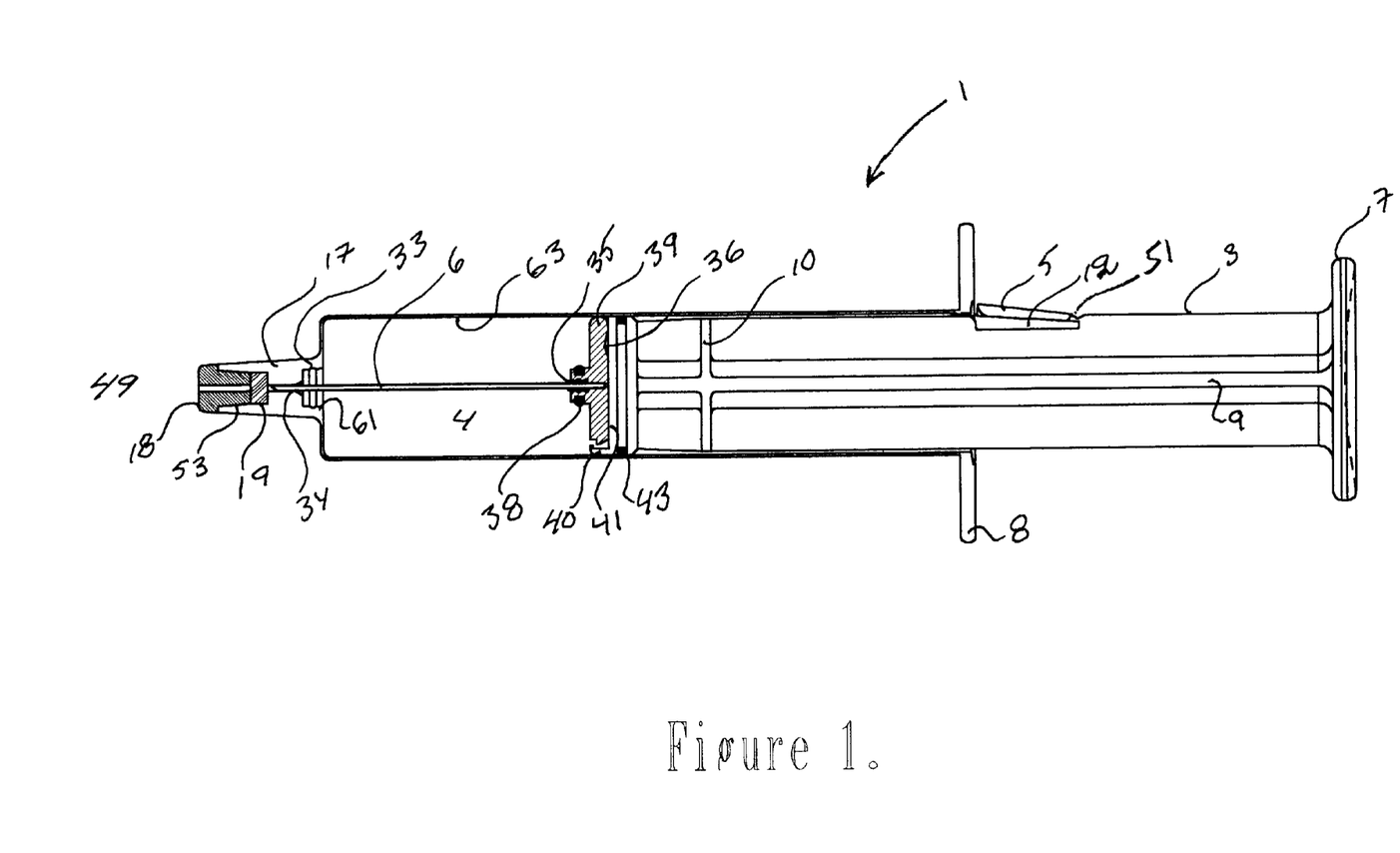
FIG. 1 is a partial sectional view along a plane parallel to the longitudinal axis of an embodiment of the hypodermic injection device with the piston in the initial position.

FIGS. 1 through 6 show the basic structure, assembly, and mode of operation of hypodermic injection device 1 of the present invention. FIG. 1 illustrates the initial state of device 1 when delivered, for example, in a sterile package to the user of injection device 1. Hypodermic device 1 as illustrated in FIG. 1 is comprised of barrel 2, piston 3, reservoir 4, lock 5, and needle 6. Barrel 2 has a proximal 48 open end 59, an outer wall 47, an inner wall 63, and a luer sleeve 17 on its distal 49 end. Piston 3 has a longitudinal stem 64 with at least one longitudinal rib 9 in parallel alignment with the central axis 60 of barrel 2. Piston diameter 69 is the distance from the center of piston 3 to the outer-most wall of the combination of stem 64 and a rib 9. Needle 6 may be a 300 Series made of stainless steel, but any needle having a nozzle 30, a bore 32, and an inlet 31 may be suitable, depending upon the application. Piston 3 is locked in the position shown in FIG. 1 by lock 5. Lock 5, as shown in FIG. 1, may be integrally molded into and a part of piston 3. Piston 3 and barrel 2 may be plastic molded elements, using conventional plastic molding techniques. The types of plastics suitable for injection device 1 are, for example, polycarbonate and polypropylene. These plastics are commercially available and currently used in the manufacture of hypodermic injection devices. These types of materials are sufficiently impact resistance to withstand the normal forces and usage experienced in the medical environment without sustaining damage. Substitute materials are also readily available for manufacture of device 1 for use in other more demanding environments or for uses other than medical, such as in the research laboratory, outdoor use, or for use in conjunction with injecting lubricants, adhesives, and other fluids of varying viscosities. With lock 5 in its normal position, i.e., its molded in position, it is raised above the outside diameter of piston 3 so that lock 5 extends beyond the inside diameter of barrel 2. In this normal position, the distal end of lock 5 engages with the proximal end of barrel 2, at the junction with barrel grip 8, so that piston 3 cannot not be slid into barrel 2 by axial force on piston 3 in the direction of the distal end of barrel 2. The term distal is used to refer to the needle 6 end of hypodermic device 1 of the present invention. The term proximal is used to refer to the other end of device 1. Lock 5 is attached to piston 3 by tab 51. Tab 51 is of a thickness that allows lock 5 to be relatively easily depressed by the user's finger when using injection device 1, yet thick enough that it will not be accidentally depressed during normal shipping, handling, and manipulation of device 1. In other words, it is of a thickness that requires a conscientious effort to depress it. Upon depression, lock 5 moves into lock depression space 12. Space 12 is of sufficient depth that when lock 5 is fully depressed it seats in space 12 so that the upper surface of lock 5 is at or below the outside diameter of piston 3, thereby allowing the piston to be slid into barrel 2. Since lock 5 is molded in the normally up position, i.e., at least the distal end of lock 5 is extended beyond the outside diameter of piston 3, it has memory in that it returns to the normally up position when any downward force on the lock is relieved. The downward force is relieved when the user's finger pressure ceases or when piston 3 is pulled in a proximal direction relative to barrel 2 to the point that the distal end of lock 5 extends beyond the inner wall of barrel 2, thereby once again locking piston 3 so that it cannot be extended into the barrel without further downward pressure on lock 5. As shown in FIG. 7A, the surface of lock 5 adjacent the outer wall of piston 3 is curved on the same radius as the outer wall of piston 3, which is the same radius as the inner wall of barrel 2. This allows for smooth travel of piston 3 into barrel 2.

Piston 3 locking feature of this invention prevents accidental extension of needle 6, as will be explained more fully in this written disclosure. If needle 6 is accidentally extended, it may be exposed to harmful pathogens or other substances or be damaged by blunting, bending, or scraping forces occurring in the working environment. More importantly, the exposure of needle 6, except when it must be extended for injection of a fluid or withdrawal of fluids, increases the possibility of an accidental needle prick. Upon the occurrence of such a needle prick, it is often not possible to determine whether an infectious substance was on the needle. The resulting uncertainty, and in the case of AIDS months or years of waiting, whether the person experiencing the needle prick has become infected, is often the cause of untold anguish and disruption of the care giver's career. And, of course, the consequences of actual infection are often fatal and seriously life compromising during the period of sickness.

Piston grip 7 provides an ergonomic seat for the user's thumb to rest during movement of piston 3 into barrel 2. The dotted line drawn on piston grip 7 in FIG. 1 is the depression, which seats the thumb. Circumferentially placed around the outside periphery or stem 64 of piston 3 are four longitudinal ribs 9. Ribs 9 provide structural strength to piston 3. Ribs 9 allow the piston 3 to be molded using less material than would be used if piston 3 diameter were substantially equal to the inside diameter of barrel 2 completely around the piston's entire circumference and along piston's entire length. Additionally, the added friction between the surface of the outside diameter of piston 3 and the inside diameter of barrel 2, would require greater force to be applied to piston 3 to move piston 3 distally into barrel 2. With only ribs 9 providing contact with the inside surface of barrel 2, less force is required for movement of piston 3.

Barrel grip 8 provides the user with a means to grip barrel 2 when depressing piston 3 into barrel 2. The user's fingers grip the distal side of barrel grip 8 and the thumb depresses piston 3.

Piston rings 10 provide for circumferential support for piston 3 within barrel 2. The periphery of faceplate 41 also functions to provide circumferential support. The additional support and the added friction assists with the smooth and tight fitting movement of piston 3 within barrel 2. Since each piston ring 10 is relatively narrow, the added friction is not great enough to require excessive force by the user to extend piston 3 into barrel 2. Gasket 43 in gasket channel 67 provides a fluid resistant seal between fluid reservoir 4 and the interface between piston 3 and barrel 2 and thereby avoids leakage of the fluid along that interface.

Support plate 39 supports the proximal end of needle 6 within barrel 2. Needle 6 is affixed, by for example an adhesive bonding material 35, into a bonding recess 66 in support plate 39. Support plate 39 is positioned relative to face plate 41 by the mating engagement of concave location boss 37 on support plate 39 with convex location boss 36 on face plate 41 as illustrated in FIGS. 8A, 9A–C, and 10A–C.

Reservoir 4 for the fluid to be injected or the fluid to be withdrawn is formed in the distal interior end of barrel 2. The distal end of reservoir 4 terminates in luer sleeve 17 and the proximal end terminates in the combination of support plate 39 and faceplate 41. The longitudinal dimension of reservoir 4 varies with the position of the piston 3 within the barrel 2.

Figure 7A:
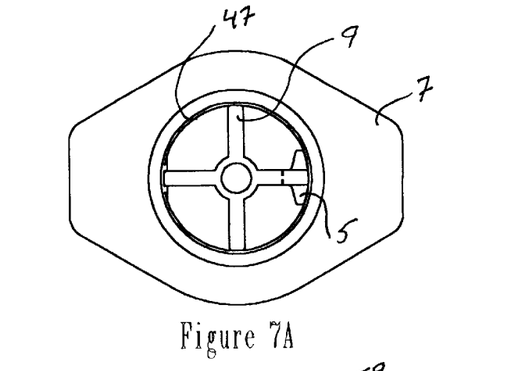
FIG. 7A is a plan view of the proximal end of the barrel of an embodiment of the hypodermic injection device of the present invention.
Figure 7B:
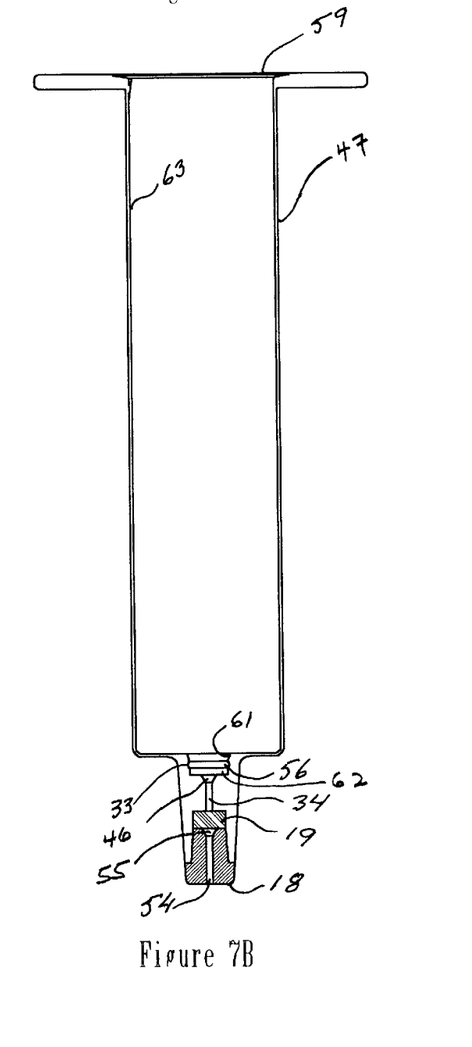
FIG. 7B is an axial cross section view of the barrel of an embodiment of the hypodermic injection device of the present invention.

The distal end of needle 6 is supported by a guide-way 52. Guide-way 52 may be of any structure that supports the distal end of needle 6 in a first or initial position as shown in FIG. 1 and during extension of needle 6 out of the distal end of hypodermic device 1 or during retraction of needle 6 into device 1. In one embodiment, guide-way 52 collectively comprises, as shown in FIG. 7B, support plate plug guide-way 33, needle guide-way 34, septum 19 after perforation by extension of needle 6, end cap needle pilot 55, and end cap guide-way 54. Support plate plug guide-way 33 collectively comprises a proximal first diameter 61, an O ring detent 56, a second diameter 62, and support plate plug needle pilot 46.

End cap 18 and septum 19 are inserted into luer sleeve cavity 53. End cap 18 and septum 19 may either be friction fitted into luer sleeve cavity 53 or bonded into cavity 53. End cap 18 may be made of the same material from which barrel 2 and piston 3 are made or other suitable material that will allow end cap 18 to non-releasably fit into luer sleeve cavity 53. End cap 18 exists to fixedly retain septum 19. Septum 19 may be made of the same or similar material as used on a vial of an injectable drug. The septum of a drug vial allows the needle of a hypodermic injection device, such as the invention described in this written description, to be inserted through it for the purpose of withdrawing the medical fluid in the vial up into the injection device. Upon removal of all or a portion of the fluid from the vial, the septum seals itself, thereby maintaining the fluid safe from the environment and exposure to contamination. The septum serves the same purpose in the injection device of the present invention 1. Septum 19 is a barrier that maintains reservoir 4 free from contaminants. But, it is a barrier that is easily penetrated by needle 6 when the user extends piston 3 in a distal direction to fully extend needle 6. Septum 19 is usually a silicone rubber material.

End cap 18 has end cap needle guide-way 54 axially aligned with needle guide-way 34, which in turn is axially aligned with central axis 60 of barrel 2. End cap 18 is also provisioned with end cap needle pilot 55 for guiding needle 6 into end cap needle guide-way 54 as illustrated in FIG. 7B.

Figure 2:
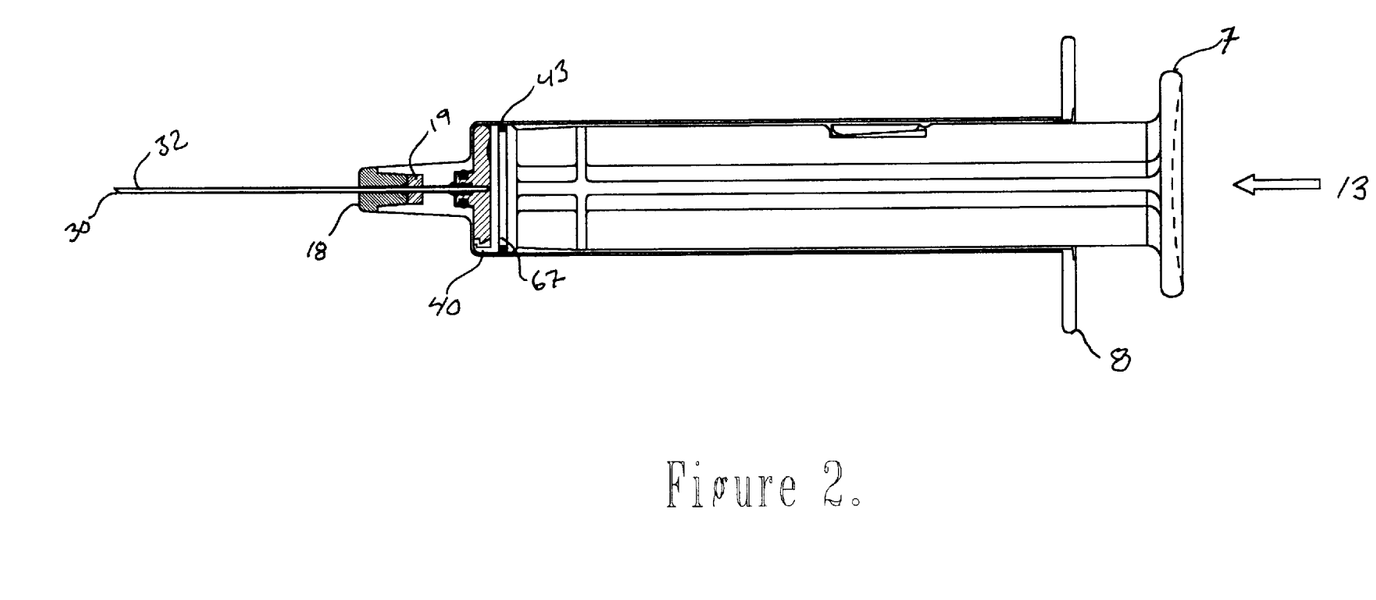
FIG. 2 is a partial sectional view along a plane parallel to the longitudinal axis of an embodiment of the hypodermic injection device with the piston in the full needle extension position.

FIG. 2 illustrates hypodermic device 1 with needle 6 in the fully extended position. Lock 5 is shown inside barrel 2 in a fully depressed position seated in lock depression space 12, thereby allowing piston 3 to slide within barrel 2. Distal end 49 of needle 6 with its open end or nozzle 20 is out of its protective reservoir 4 portion of the enclosed barrel 2 and piston 3 combination. Needle 6 has penetrated septum 19 on its excursion through needle guide-way 34 and then end cap needle guide-way 54. Support plate plug 45 (comprising a first diameter 70, an o-ring channel 65 containing an o-ring 38, and a second diameter 72) is extended into and mates with support plate plug guide-way 33, thereby assisting the centering of needle 6 in needle guide-way 34 and, upon extension of piston 3 and perforation of septum 19, end cap needle pilot 55, and end cap needle guide-way 54.

Figure 3:
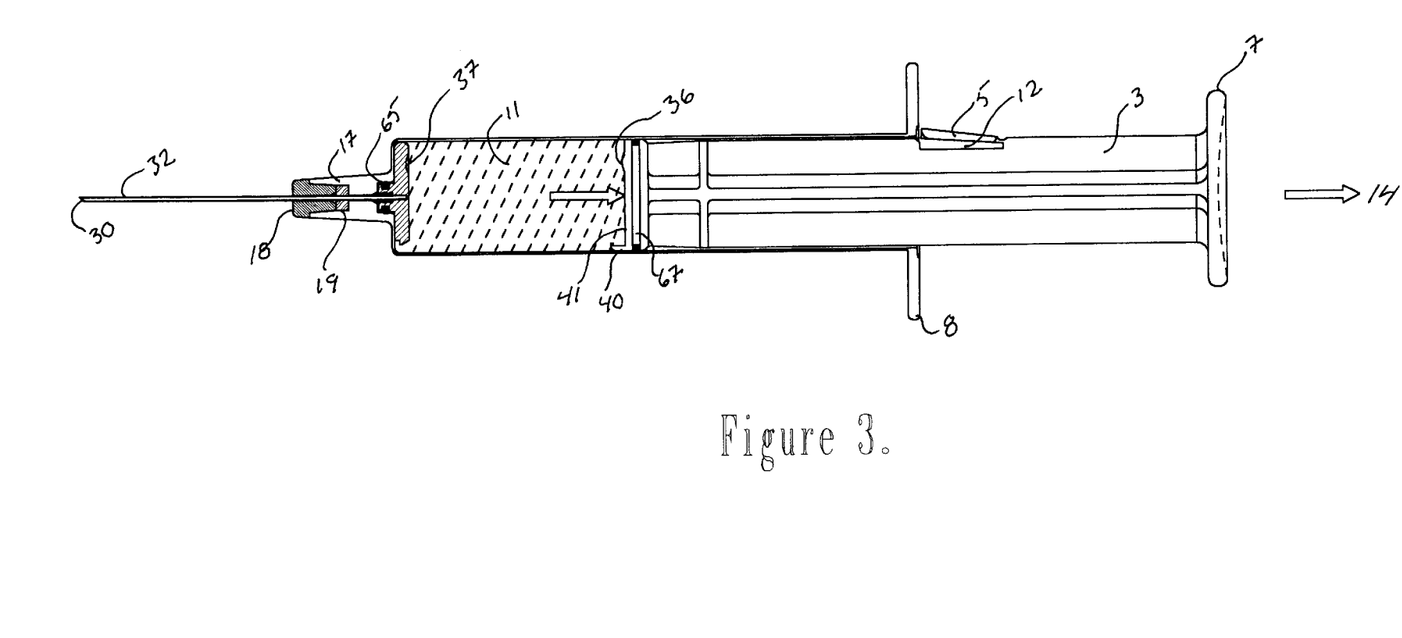
FIG. 3 is a partial sectional view along a plane parallel to the longitudinal axis of an embodiment of the hypodermic injection device with the piston in the full fluid reservoir position.

FIG. 3 illustrates hypodermic device 1 after the piston 3 has been retracted, thereby filling reservoir 4. With piston 3 fully retracted, lock 5 is automatically raised to its normal position, due to the memory of the material from which it is fabricated, out of lock depression space 12 and prevents piston 3 from once again being moved distally into barrel 2, safely preventing the accidental discharge of the fluid in reservoir 4. FIG. 3 illustrates that faceplate 41 and support plate 39 are not fixed or hooked to one another while in the positions shown in FIGS. 1 through 3. Support plate 39 freely rides in barrel 2 since it has a diameter substantially equal to or less than the inside diameter of barrel 6. Support plate 39 is forced distally by faceplate 41 when piston 3 is moved distally. However, upon retraction of piston 3, support plate 39 remains firmly, but removably fixed in support plate plug guide-way 33 with assistance from the mating engagement of O ring 38 with O ring detent 56. Engagement of o-ring 38 and o-ring detent 56 also provides a fluid and airtight seal, preventing fluid in reservoir 4 from leaking out around needle 6 or air to leak into reservoir 4. Retraction of piston 3 results in suction within reservoir 4, allowing fluid to flow through nozzle 20, into bore 32, and through inlet 31 of needle 6 to fill reservoir 4, as further illustrated in FIG. 9B. Without the airtight seal provided by o-ring 38 and o-ring detent 56 combination, the necessary suction to draw in the fluid would be compromised.

Figure 4A:
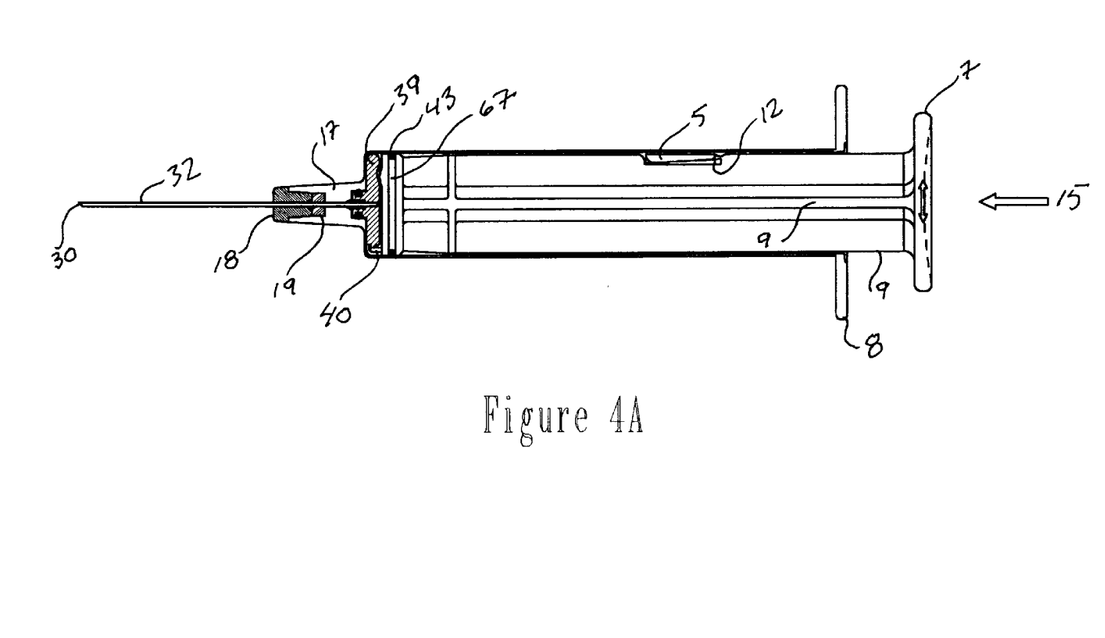
FIG. 4A is a partial sectional view along a plane parallel to the longitudinal axis of an embodiment of the hypodermic injection device with the piston in the empty fluid reservoir position.

FIG. 4A illustrates hypodermic device 1 with piston 3 fully extended into barrel 2. Full extension has resulted in the injection of all of the fluid in reservoir 4 into a thing 68, which may be a patient. Prior to injection, lock 5 must be depressed as described in connection with FIG. 1. FIGS. 4A and 2 are similar. A difference between the two figures surrounds the position of hook 40 relative to undercut 42 on support plate 39, as shown in more detail in FIGS. 8A, 8B and 9B. After injection of the fluid by moving piston 3 distally into barrel 2, the user then twists piston 3 clockwise or counter clockwise until hook 40 engages with undercut 42, which is located on the distal face of support plate 39.

Figure 4B:
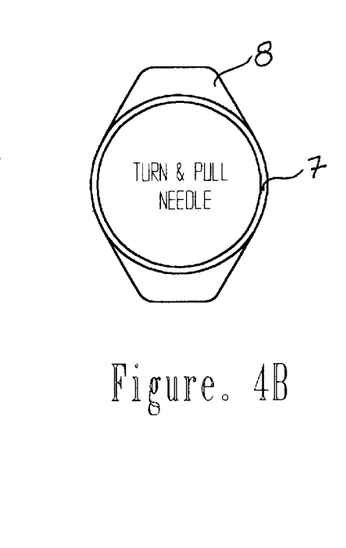
FIG. 4B is an end view of the piston grip of an embodiment of the hypodermic injection device illustrating an exemplar of directions for user to follow after injection of the fluid is completed.
Figure 5:
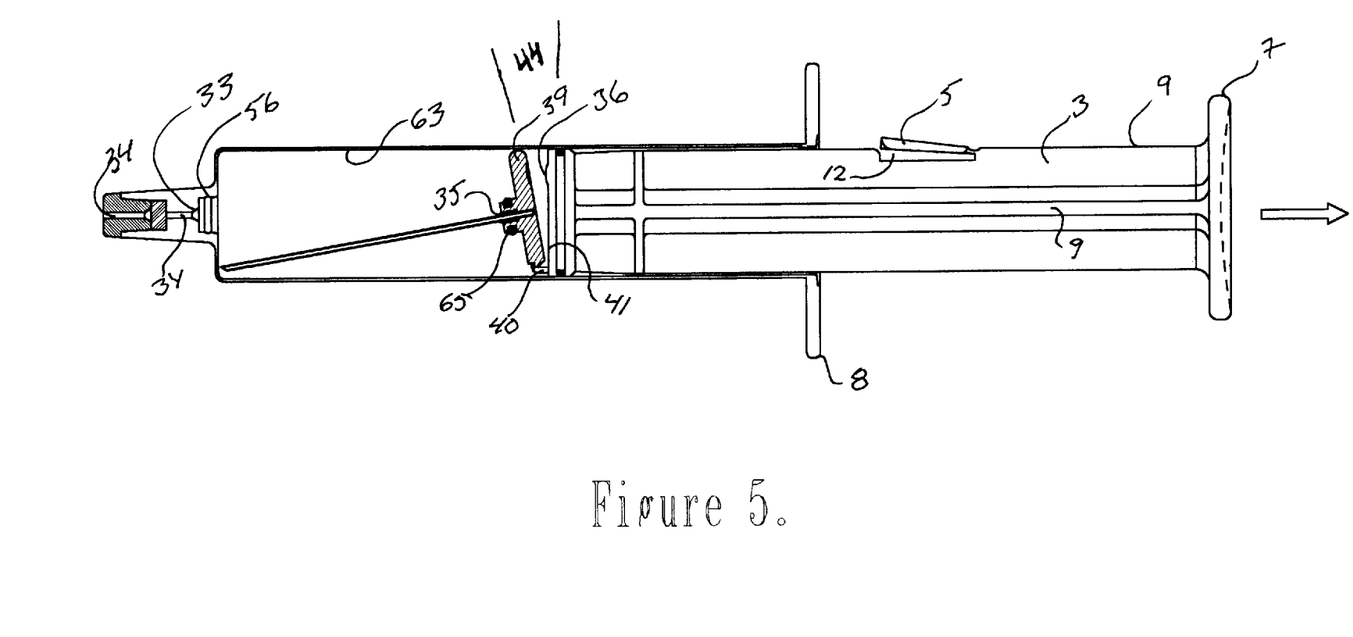
FIG. 5 is a partial sectional view along a plane parallel to the longitudinal axis of an embodiment of the hypodermic injection device in its final state of use and ready for disposal.
Figure 8A:
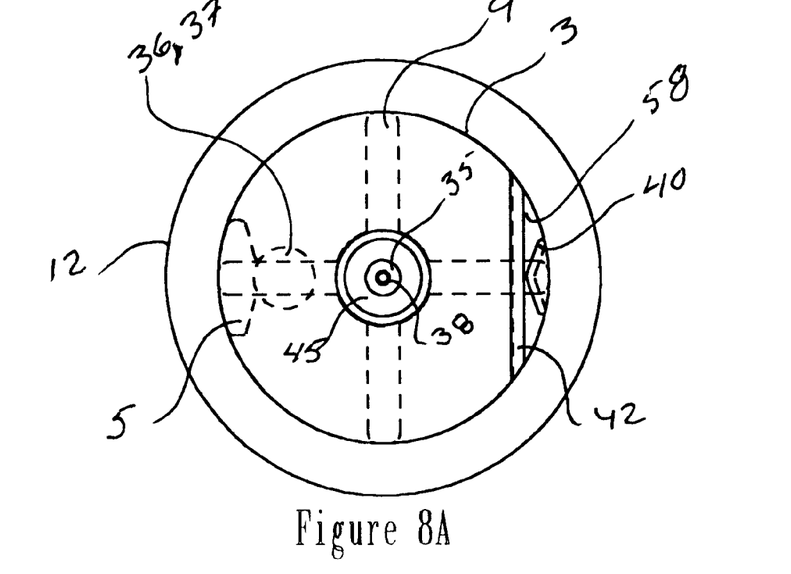
FIG. 8A is a plan view of the distal end of the barrel of an embodiment of the hypodermic injection device of the present invention showing a first position with the support plate unhooked.
Figure 8B:
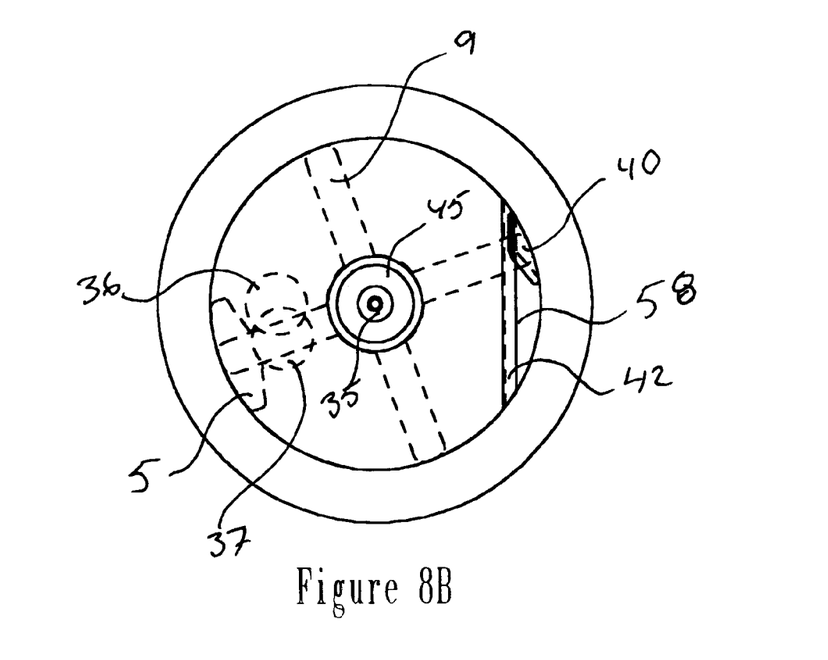
FIG. 8B is a plan view of the distal end of the barrel of an embodiment of the hypodermic injection device of the present invention showing a second position with the support plate hooked.
Figure 9A:
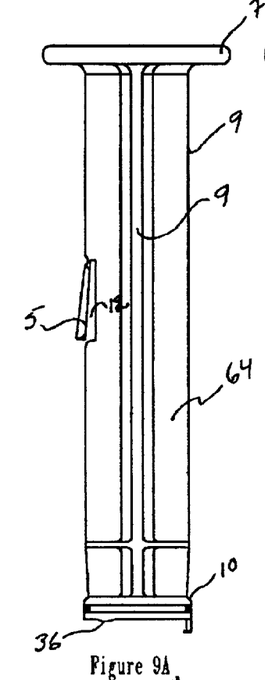
FIG. 9A is a view of the piston of an embodiment of the hypodermic injection device of the present invention in a first position.
Figure 9B:
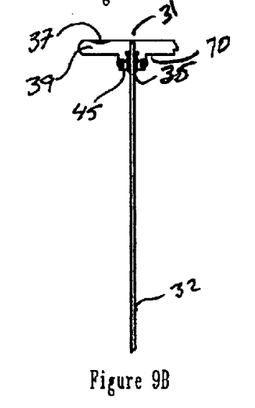
FIG. 9B is a view of the needle and support plate of an embodiment of the hypodermic injection device of the present invention corresponding with the first position shown in FIG. 9A.
Figure 9C:
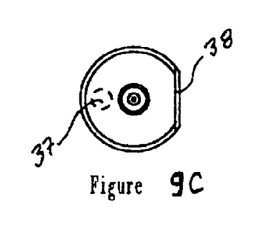
FIG. 9C is a top view of the distal end of the support plate of an embodiment of the hypodermic injection device of the present invention corresponding with the first position shows in FIGS. 9A and 9B.
Figure 10A:
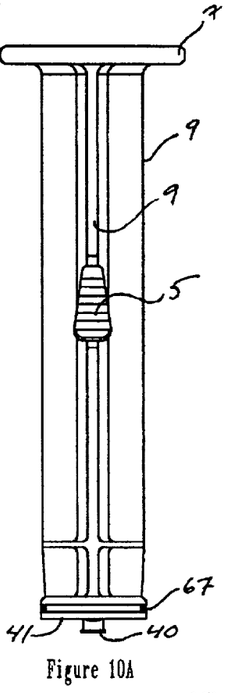
FIG. 10A is a view of the piston of an embodiment of the hypodermic injection device of the present invention rotated 90 degrees from the view shown in FIG. 9A.
Figure 10B:
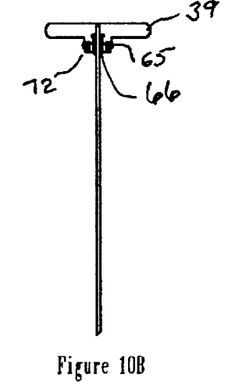
FIG. 10B is a view of the needle and support plate of an embodiment of the hypodermic injection device of the present invention corresponding with the position shown in FIG. 10A.
Figure 10C:
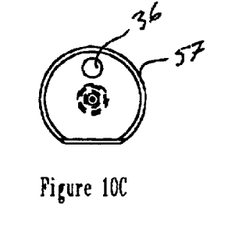
FIG. 10C is a top view of the proximal end of the support plate of an embodiment of the hypodermic injection device of the present invention corresponding with the position shown in FIG. 10A.

Upon retraction of piston 3, support plate 39 is pulled along with piston in the proximal direction by hook 40 on faceplate 41. Another difference between FIGS. 4A and 2 is the position of convex location boss 36 and concave location boss 37 relative to one another. In FIG. 2, both bosses 36 and 37 were matingly engaged. In FIG. 4A they are do not mate. They have moved out of alignment due to the twist of piston 3 relative to the position of barrel 2. FIGS. 8A and 8B illustrate the change of positions of these two bosses 36 and 37 relative to one another other. As shown in FIG. 8B, rotation of piston 3 moves the bosses 36 and 37 relative to one another, but leaves them in an overlapped position forcing the distal end of face plate 41 to separate from the proximal end of support plate 39. The separation drives undercut 42 of support plate 39 against hook 40 and maintains it there to prevent accidental disengagement of undercut 42 and hook 40 during retraction of needle 6. FIG. 5 illustrates full retraction of needle 6. FIG. 4B illustrates an example of simple instructions marked on the proximal end of piston grip 7.

FIG. 5 illustrates injection device 1 in its final state of use and ready for disposal. Needle 6 is fully retracted by retracting piston 3 with hook 40 in engagement with undercut 42 to the point where needle 6 is fully extracted from support plate plug guide-way 33. At that point, there is nothing supporting the distal end of needle 6 and it falls down into reservoir 4 where it can no longer be extended outside barrel 2. Injection device 1 is no longer usable and is ready for disposal with needle 6 already in a sharps container, the reservoir, protecting living beings or property from damage caused by sharp needle 6.

FIG. 5 illustrates support plate 39 tilting relative to a plane perpendicular to the axis of hypodermic injection device 1. Tilt angle 44 in one embodiment approximates 10 degrees. Tilting of support plate 39 is assisted in part by the differential friction between the circumferential rim 57 of support plate 39 and barrel 2. There is no friction between support plate 39 and barrel 2 in the region of undercut 42 because undercut 42 is located on a chord 58 of support plate 39 and chord 58 does not contact barrel 2. Chord 58 is best illustrated in FIGS. 8A, 8B, 9C, and 10C. The location of chord 58 in barrel 2, shown in FIGS. 1 through 5 is located towards the bottom of each of the figures. Therefore, that area exerts the least frictional force and tipping occurs elsewhere with hook 40 and undercut 42 acting as the fulcrum.

Figure 6:
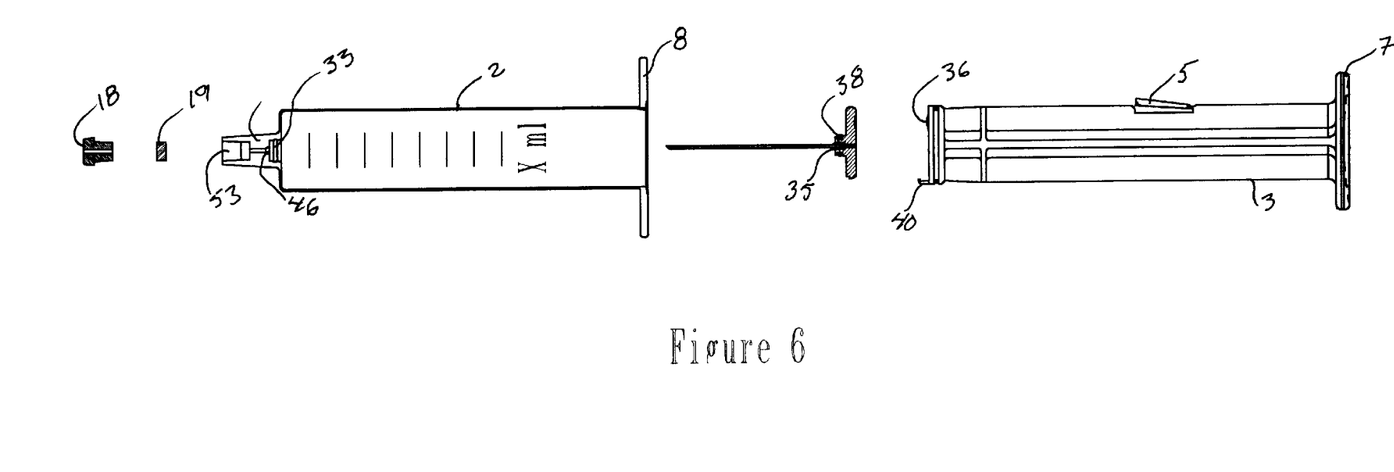
FIG. 6 is an exploded assembly view of an embodiment of the hypodermic injection device of the present invention.

FIG. 6 illustrates the generally assembly of the injection device. Various modifications and variations of this invention will become apparent to those skilled in the art without departing from the scope and spirit of this invention, and it should be understood that this invention is not to be unduly limited to the illustrative embodiment set forth in this specification.

What I claim is:

1. A hypodermic injection device, comprising: (a) a barrel having an open end and a guide-way, both in alignment with the central axis of the barrel; (b) a piston in alignment with the central axis of the barrel engaged in the barrel for axial sliding movement within the inner wall of the barrel; (c) a needle, in alignment with the central axis of the barrel with its proximal end facing the distal end of the piston and with the distal end of the needle supported in the guide-way; (d) a reservoir within the space between the distal end of the barrel and the proximal end of the needle, so that when the piston is moved distally within the barrel, the needle extends beyond the distal end of the guide-way in a position for drawing a fluid into the reservoir through the needle during subsequent retraction of the piston within the barrel; and (e) a means for engagement of the needle to the distal face of the piston, so that after insertion of the piston in the distal direction within the barrel to express the previously loaded fluid, the distal end of the needle may be fully retracted into the reservoir by retracting the piston.

2. A hypodermic injection device, comprising: (a) a barrel comprising an open end, an annular barrel grip extending in a radial direction from the barrel outer wall at the open end, a luer sleeve at the distal end of the barrel in alignment with the central axis, an end cap in the distal end of the luer sleeve in alignment with the central axis, a septum in alignment with the central axis in abutting engagement with the luer sleeve, and a guide-way in alignment with the central axis extending through the luer sleeve and the end cap, the guide-way comprising (i) a support plate plug guide-way comprised of a first diameter, an o-ring detent, a second diameter, and a support plate plug needle pilot, (ii) a needle guide-way, (iii) the septum after perforation by the needle, and (iv) an end-cap needle guide-way; (b) a piston in alignment with the central axis of the barrel engaged for axial sliding movement within the inner wall of the barrel, the piston comprising (i) a piston stem, (ii) with at least one rib extending longitudinally along the piston stem, (iii) a piston grip extending in a radial direction from the piston stem and rib combination with a diameter exceeding that of the piston stem and rib combination, (iv) a lock attached to a piston rib by a tab for depression into a depression space of a depth sufficient to allow the lock to be flush with the diameter of the piston stem and rib combination so that the piston may be extended into the barrel and may return to a normal raised position upon release of depression pressure to allow the lock to be raised beyond the diameter of the piston stem and rib combination, thereby locking the piston from axial extension into the barrel, (v) at least one piston ring, the diameter of which is substantially equivalent to the diameter of the barrel inner wall, engaged for axial sliding movement within the inner wall, (vi) a face plate on the distal end of the piston, the diameter of which is substantially equivalent to the diameter of the barrel inner wall and which is engaged with the barrel inner wall for axial sliding movement therein, the face plate having a hook at its periphery for hooking a support plate when the piston is turned within the barrel and also having a convex location boss on its distal face for engagement with a concave location boss on a proximal face of the support plate and for disengagement with the concave location boss when the piston is turned within the barrel to hook the support plate, and (vii) a gasket in a gasket channel located between an adjacent piston ring and the face plate having a diameter which is substantially equivalent to the diameter of the barrel inner wall, whereby a leak resistant seal is formed; (c) the support plate for supporting a needle in a longitudinal direction on the central axis comprised of a concave location boss located on the proximal face of the support plate for mating engagement with the convex location boss, an inlet in line with the central axis and in communication with a bore of the needle, a support plate plug for mating engagement with the support plate plug guide-way when the piston is fully extended into the barrel, the support plate plug having a first diameter, a second diameter, and an o-ring in an o-ring channel between the first and second diameter, the needle bonded into a bonding recess located in the distal face of the support plug, an undercut for engagement with the hook when the piston is turned within the barrel; (d) the needle, in alignment with the central axis of the barrel with the proximal end of the needle facing the distal end of the piston and with the distal end of the needle supported in the needle guide-way, the needle having a length such that when the piston is retracted out of the barrel beyond a locked position with respect to the barrel, the needle retracts from the needle guide-way and from the support plate plug guide-way so that the distal end of the needle is contained within the distal end of a reservoir; and (e) the reservoir in the distal end of the barrel when the piston is in the locked position in the barrel, the length of which reservoir is directly related to the longitudinal distance of the location of the lock on the piston from the face plate.

3. A method of injecting a fluid using the hypodermic injection device of claim 2, comprising the steps of: (a) with the piston of the injection device in its first position wherein the piston is locked into an initial position longitudinally with respect to the barrel and the distal end of the needle is supported in the needle guide-way, depressing the lock and then sliding the piston in a distal direction into the barrel to the distal end of the barrel, so that the needle is extended beyond the distal end of the end cap; (b)extending the needle into a fluid to be injected; (c) retracting the piston in the proximal direction until the lock engages the proximal end of the barrel, so that the fluid is drawn into the reservoir; (d) inserting the needle into the thing to be injected; (e) depressing the lock and then sliding the piston in a distal direction into the barrel to the distal end of the barrel, so that the fluid in the reservoir is injected into the thing to be injected; (f) turning the piston in the barrel to engage the piston hook with the support plate undercut; and (g) retracting the piston from the barrel in a proximal direction to a point where the lock is beyond the barrel open end, so that the distal end of the needle is within the reservoir.

4. A hypodermic injection device comprising: (a) a barrel; (b) a piston engaged in the barrel for axial sliding movement therein; (c) a reservoir; (d) a needle, the distal end of the needle supported in a needle guide-way, the proximal end of the needle facing the distal end of the piston for abbutable contact therewith, and the needle of a length that will allow the needle to be contained in the reservoir when the distal end of the needle is retracted from the guide-way; and (e) a means of engagement of the proximal end of the needle with the distal end of the piston for retraction of the distal end of the needle from the guide-way.

5. The hypodermic injection device of claim 4, in which the piston further comprises a manually depressible lock attached to the piston for manual depression into a depression space, the depth of the depression space sufficient to allow the lock when depressed to be flush with the piston diameter thereby allowing the piston to extend into the barrel, and upon retraction of the piston from the barrel, the lock is automatically returnable to its normally raised position upon release of the depression pressure of the inner wall so the piston is again locked from axial extension into the barrel.

6. The hypodermic injection device of claim 5, in which the piston further comprises (i) a piston stem, (ii) with at least one rib extending longitudinally along the piston stem, (iii) a piston grip extending in a radial direction from the piston stem and rib combination with a diameter exceeding that of the piston stem and rib combination, (iv) at least one piston ring, the diameter of which is substantially equivalent to the diameter of the inner wall, engaged for axial sliding movement within the inner wall, and (v) a gasket in a gasket channel located between an adjacent piston ring and the face plate having a diameter which is substantially equivalent to the diameter of the barrel inner wall, whereby a leak resistant seal is formed.

7. The hypodermic injection device of claim 5, in which the means of engagement of the proximal end of the needle with the distal end of the piston for retraction of the distal end of the needle from the guide-way further comprises: (a) a face plate on the distal end of the piston with a hook at the periphery of the face plate for hooking a support plate when the piston is turned within the barrel and (b) a support plate, for supporting the needle in a longitudinal direction on a central axis, comprised of an inlet in line with the central axis and in communication with a bore of the needle and the proximal face of the support plate, a support plate plug for mating engagement with a support plate plug guide-way when the piston is fully extended into the barrel, the needle bonded into a bonding recess located in the distal face of the support plug, an undercut for engagement with the hook when the piston is turned within the barrel.

8. A method of injecting a fluid using the hypodermic injection device of claim 7, comprising the steps of: (a) beginning with the lock is in its normal position locking the piston into the a position longitudinally with respect to the barrel and the distal end of the needle supported in the needle guide-way, depressing the lock and then sliding the piston in a distal direction into the barrel to the distal end of the barrel, so that the needle is extended beyond the distal end of the end cap; (b) extending the needle into a fluid to be injected; (c) retracting the piston in the proximal direction until the lock engages the proximal end of the barrel, whereby the fluid is drawn into the reservoir; (d) inserting the needle into the thing to be injected; (e) depressing the lock and then sliding the piston in a distal direction into the barrel to the distal end of the barrel, whereby the fluid in the reservoir is injected into the thing to be injected; (f) turning the piston in the barrel to engage the piston hook with the support plate undercut; and (g) retracting the piston from the barrel in a proximal direction to a point where the lock is beyond the barrel open end until the distal end of the needle is within the reservoir.

9. The hypodermic injection device of claim 5, wherein the reservoir comprises the space between the distal end of the barrel and the distal end of the piston when the piston is in the locked position in the barrel.

10. The hypodermic injection device of claim 4, in which the means of engagement of the proximal end of the needle with the distal end of the piston for retraction of the distal end of the needle from the guide-way further comprises: (a) a face plate on the distal end of the piston with a hook at the periphery of the face plate for hooking a support plate when the piston is turned within the barrel; and (b) a support plate, for supporting the needle in a longitudinal direction on the central axis, comprised of an inlet in line with the central axis and in communication with a bore of the needle and the proximal face of the support plate, a support plate plug for mating engagement with a support plate plug guide-way when the piston is fully extended into the barrel, the needle bonded into a bonding recess located in the distal face of the support plug, and an undercut for engagement with the hook when the piston is turned within the barrel.

11. The hypodermic injection device of claim 10, also comprising a convex location boss on the distal face of the face plate and a concave location boss on the proximal face of the support plate for mating engagement of the location bosses when the piston is in a first radial position relative to the barrel and for disengagement of the location bosses when the piston is turned within the barrel into a second radial position relative to the barrel, so that, the support plate is tipped along a portion of its periphery away from the face plate.

12. The support plate of claim 10, also comprising a first diameter, a second diameter, and an o-ring in an o-ring channel between the first and second diameter.

13. The hypodermic injection device of claim 4, in which the barrel is comprised of an open end, an annular barrel grip extending in a radial direction from the barrel outer wall at the open end, a luer sleeve at the distal end of the barrel in alignment with the central axis of the barrel, an end cap in the distal end of the luer sleeve in alignment with the central axis, a septum in alignment with the central axis in abutting engagement with the luer sleeve, and a guide-way in alignment with the central axis extending through the luer sleeve and the end cap, the guide-way comprising (i) a support plate plug guide-way comprised of a first diameter, an o-ring detent, a second diameter, and a support plate plug needle pilot, (ii) a needle guide-way, (iii) the septum upon perforation by the needle, and (iv) an end-cap needle guide-way.

* * * * *